United States Patent [19]

Grice

[11] Patent Number: 5,387,227
[45] Date of Patent: Feb. 7, 1995

[54] METHOD FOR USE OF A LAPARO-SUTURE NEEDLE

[76] Inventor: O. Drew Grice, 701 Newman Rd., New Bern, N.C. 27562

[21] Appl. No.: 944,205
[22] Filed: Sep. 10, 1992
[51] Int. Cl.⁶ .................................................. A61B 17/00
[52] U.S. Cl. ............................................ 606/222; 606/139; 606/148; 606/184; 606/223; 606/144; 128/898; 223/104
[58] Field of Search ................. 606/139, 144, 145, 147, 606/148, 181, 182, 184, 185, 187, 189, 222, 223, 224; 163/5; 223/102, 104; 128/898; 604/164

[56] References Cited

U.S. PATENT DOCUMENTS

| | | | |
|---|---|---|---|
| 683,655 | 10/1901 | Mersch | 223/104 |
| 1,539,221 | 5/1925 | Tennant | 606/147 |
| 2,496,111 | 9/1947 | Turkel . | |
| 2,579,192 | 8/1950 | Kohl . | |
| 2,738,790 | 3/1956 | Todt, Sr. et al. | 606/145 |
| 2,811,971 | 11/1957 | Scott . | |
| 3,154,229 | 6/1961 | Mount . | |
| 3,716,058 | 2/1973 | Tanner, Jr. . | |
| 3,834,599 | 9/1974 | Herr . | |
| 3,871,379 | 3/1975 | Clarke . | |
| 3,877,434 | 4/1975 | Ferguson et al. . | |
| 3,995,619 | 12/1976 | Glatzer | 128/2 B |
| 4,221,212 | 9/1980 | Miller . | |
| 4,235,238 | 11/1980 | Ogiu et al. | 606/145 |
| 4,243,048 | 1/1981 | Griffin . | |
| 4,372,302 | 2/1983 | Åkerlund . | |
| 4,378,019 | 3/1983 | Yamada | 606/187 |
| 4,382,444 | 5/1983 | Malmin . | |
| 4,392,495 | 7/1983 | Bayers . | |
| 4,406,237 | 9/1983 | Eguchi et al. . | |
| 4,440,171 | 4/1984 | Nomoto et al. . | |
| 4,465,070 | 8/1984 | Eguchi . | |
| 4,493,323 | 1/1985 | Albright et al. . | |
| 4,602,635 | 7/1986 | Mulhollan et al. . | |
| 4,603,560 | 8/1986 | Pietrowski . | |
| 4,712,545 | 12/1987 | Honkanen . | |
| 4,723,546 | 2/1988 | Zagorski . | |
| 4,781,190 | 11/1988 | Lee . | |
| 4,784,139 | 11/1988 | Demos . | |
| 4,838,282 | 6/1989 | Strasser et al. | 606/184 |
| 4,874,375 | 10/1989 | Ellison | 604/164 |
| 4,957,498 | 9/1990 | Caspari et al. . | |
| 4,974,758 | 12/1990 | Wünsch . | |
| 4,976,269 | 12/1990 | Mehl . | |
| 5,015,250 | 5/1991 | Foster | 606/147 |
| 5,022,550 | 3/1991 | Li . | |
| 5,036,860 | 8/1991 | Leigh et al. . | |
| 5,059,201 | 10/1991 | Asnis | 606/148 |
| 5,085,661 | 2/1992 | Moss . | |
| 5,149,329 | 9/1992 | Richardson | 604/272 |
| 5,281,237 | 1/1994 | Gimpelson . | |

FOREIGN PATENT DOCUMENTS

| | | | |
|---|---|---|---|
| 2908695 | 9/1980 | Germany | 606/144 |
| 969254 | 10/1982 | U.S.S.R. | 606/144 |
| WO90/03766 | 4/1990 | WIPO . | |

OTHER PUBLICATIONS

English Translation of Bergmann German Patent No. 2,908,695.
Arthroscopy Cheater ™ American Design Group, Inc., Product Brochure undated.
English Translation of Kume Russian Patent 969,254.

Primary Examiner—Stephen C. Pellegrino
Assistant Examiner—Jeffrey A. Schmidt
Attorney, Agent, or Firm—William A. Birdwell & Associates

[57] ABSTRACT

A laparo-suture needle and method for use thereof. A medical suturing instrument employs an outer, hollow shaft having a laterally-disposed, elongate handle at a proximal end and an elongate, inner shaft disposed within the outer shaft. The inner shaft has a cutting edge at the distal end and extends out of the outer shaft at the proximal end, terminating in a spring-loaded push button. A lateral notch is formed in the inner shaft proximal of the cutting edge. The spring forces the inner shaft rearwardly so as to pull the notch within the outer shaft. By gripping the handle and placing pressure on the push button, the inner shaft is moved forward so as to expose the notch. A suture may then be placed in the notch so that the instrument grips the suture between the outer shaft and the inner shaft when the push button is released. The instrument is used for suturing muscle at an incision by gripping the end of a suture, forcing the distal end of the instrument beneath the epidermis within an incision, into the fatty tissue and through the muscle adjacent one side of the incision to force the suture through the muscle.

25 Claims, 2 Drawing Sheets

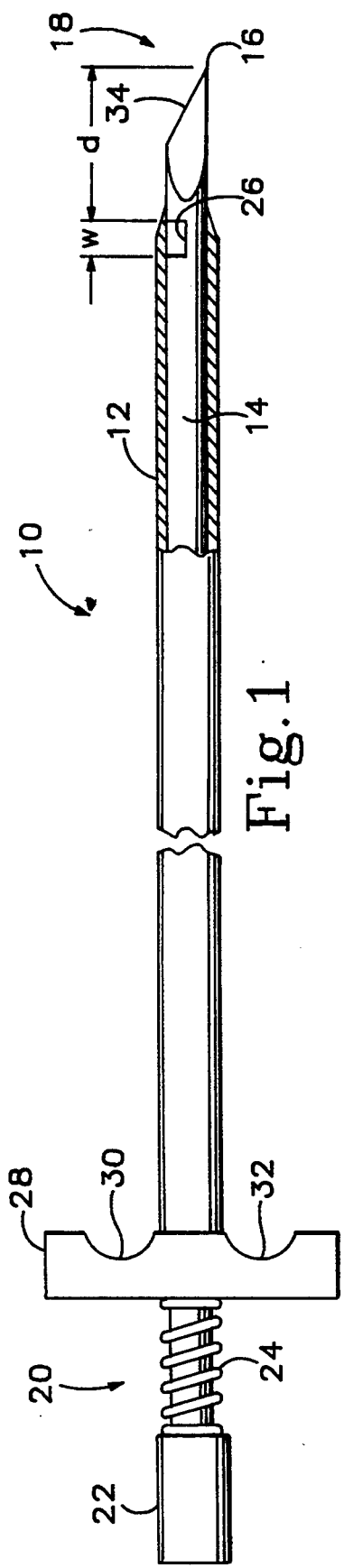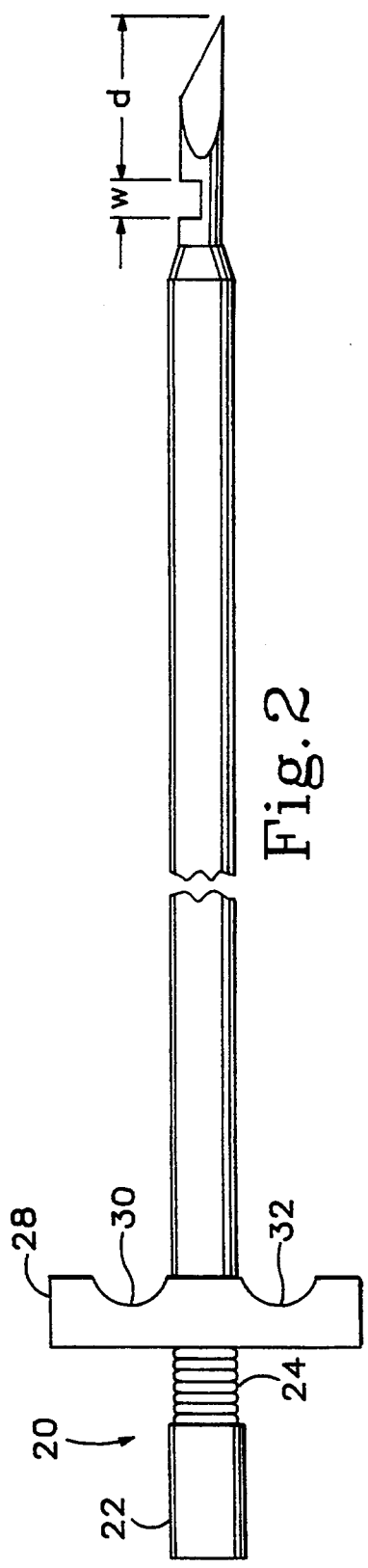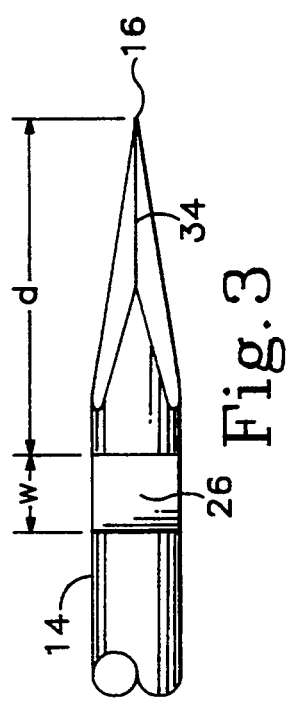

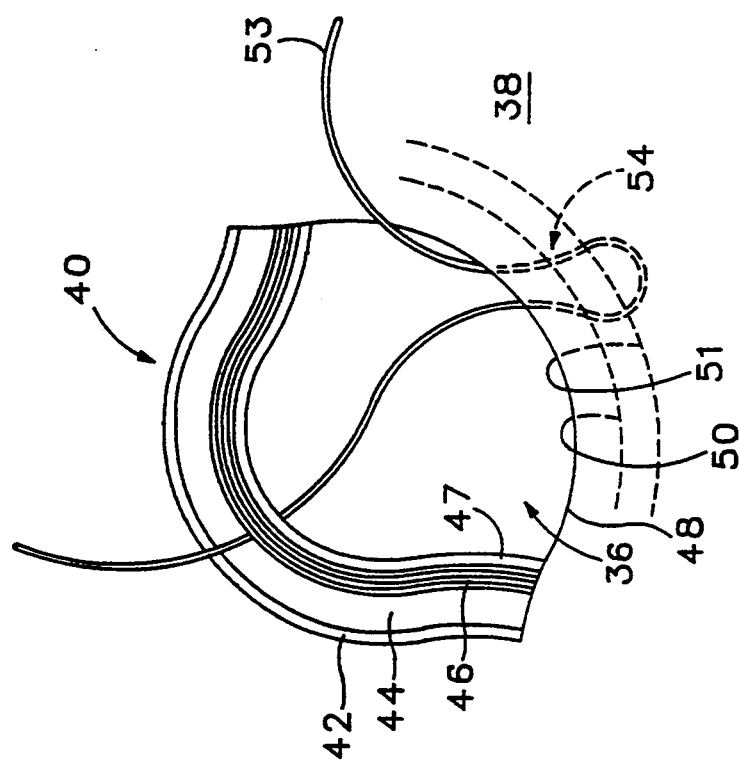
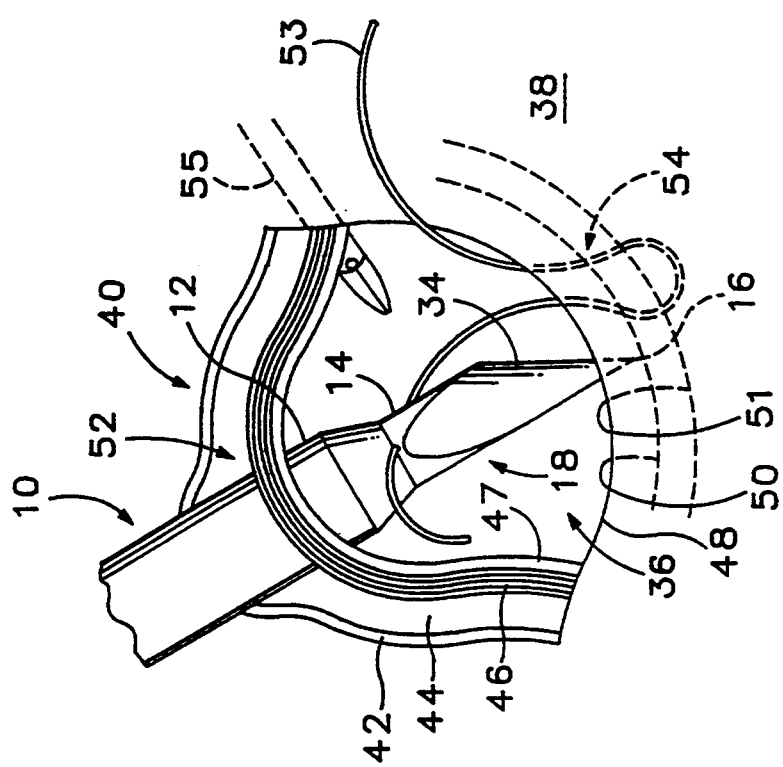

METHOD FOR USE OF A LAPARO-SUTURE NEEDLE

BACKGROUND OF THE INVENTION

This invention relates to instruments and methods for suturing tissue, particularly for suturing abdominal (laparo) muscle tissue and the lining of the abdominal cavity following abdominal, especially laparoscopic, surgery.

In performing laparoscopic surgery, it is necessary to make an incision through several layers of tissue. They are the outer layer of skin, or epidermis, a layer of fat beneath the epidermis, a layer of abdominal muscle tissue beneath the fat and the lining of the abdominal cavity, called the peritoneum. Once the procedures within the abdomen are complete, it is necessary to close the wound resulting from the incision. This has customarily been done merely by suturing the incision through the layer of epidermis. Closure of the skin does not close the muscle or the peritoneum. While the muscle and peritoneum will eventually heal, it is possible for the intestinal and fatty contents of the cavity to protrude through the opening thereby creating a hernia. Closure of the muscle and peritoneum eliminates such risk.

Therefore, it is desirable first to suture the peritoneum and the layer of abdominal muscle and thereafter to suture the layer of epidermis. However, this is difficult to accomplish with a conventional suture needle, even a curved suture needle, because the incision in the skin is small. Exposure of the incision in the muscle requires making the skin incision several times larger, defeating the concept of minimal invasion. It is difficult to manipulate a standard needle into the edges of the underlying muscle through the small incision in the skin and underlying fat tissue.

Accordingly, there is a need for an improved medical instrument and method for suturing the abdominal muscle tissue and peritoneum at an incision therethrough.

SUMMARY OF THE INVENTION

The present invention meets the aforementioned need and solves the aforementioned problems by providing a novel and improved medical instrument for suturing muscle tissue, particularly the abdominal muscle tissue together with the peritoneum. It employs an outer, hollow shaft having a laterally-disposed, elongate handle at a proximal end and an elongate, inner shaft disposed within the outer shaft. The inner shaft is solid, but flexible, and has a cutting edge at a distal end. It extends out of the outer shaft at the proximal end, terminating in a spring-loaded push button. A lateral notch is formed in the inner shaft adjacent the cutting edge. Ordinarily, the spring forces the inner shaft rearwardly so as to pull the notch within the outer shaft. By gripping the handle and placing pressure on the push button, the inner shaft is moved forward so as to expose the notch. A suture may then be placed in the notch so that the instrument pulls the suture inside the outer shaft and grips the suture between the outer shaft and the inner shaft when the push button is released.

The instrument is used by placing a suture into the notch, securing it by retracting the notch into the outer shaft, and forcing the needle through the fascia, muscle and peritoneum into the abdominal cavity. The suture is then grasped by another grasping instrument, such as grasping forceps, inserted into the abdominal cavity through another incision, and the suture is released from the notch by extending the inner shaft so as to move the notch forward out of the sheath. The instrument is then removed from the wound and reinserted on the opposite side of the muscle incision in the same way, except the instrument is empty. The suture previously passed through the muscle is grasped by the instrument, which is then removed from the incision, bringing the suture with it.

Therefore, it is a principle object of the present invention to provide a novel and improved suturing instrument and suturing method.

It is another object of the present invention to provide a suturing instrument which facilitates suturing the abdominal muscle tissue and peritoneum at an incision.

It is a further object of the present invention to provide a suturing instrument which facilitates manipulation of a suture inside the abdomen of a patient so as to guide the suture through muscle tissue on one side of an incision, grasp it within the abdomen, and pull it out through muscle tissue on the other side of the incision.

It is yet another object of the present invention to provide a method of manipulating a suture through the abdominal muscle, into the abdominal cavity, without enlarging the associated skin incision solely for the purpose of manipulating needles to suture the muscle layers of the incision.

The foregoing and other objects, features and advantages of the invention will be more readily understood upon consideration of the following detailed description of the invention, taken in conjunction with the accompanying drawings.

BRIEF DESCRIPTION OF THE DRAWINGS

FIG. 1 shows a side view of a medical instrument according to the present invention, in partial section.

FIG. 2 shows a side view of a medical instrument according to the present invention with an inner shaft thereof forced to its forward position.

FIG. 3 shows a side view of the tip of an inner shaft of a medical instrument according to the present invention from a side facing the cutting edge thereof.

FIG. 4A shows a perspective view of a medical instrument according to the present invention, and the preferred method for use thereof to close an abdominal wound according to the present invention.

FIG. 4B shows a perspective view of the abdominal wound of FIG. 4A following use of the medical instrument according to the present invention to place one loop of a suture at the wound.

DESCRIPTION OF THE PREFERRED EMBODIMENT

Referring first to FIG. 1, a preferred embodiment of a medical instrument 10 according to the present invention comprises a needle having a first, elongate, hollow, outer shaft 12 and a second, inner shaft 14 disposed within the outer shaft 12, the inner shaft 14 having a sharp point 16 disposed at the distal end 18 thereof and being longitudinally movable within the outer shaft. The outer shaft serves as a sheath for the inner shaft.

An operating means is provided at the proximal end of the outer shaft for moving the inner shaft forward and backward. Preferably, the inner and outer shafts each have cylindrical cross sections, though it is to be recognized that other shapes could be employed without departing from the principles of the invention. The operating means comprises a push button 22 for moving the inner shaft forward relative to the outer shaft, thereby activating the instrument, and a spring 24 for returning the inner shaft to a rearward position once the push button is released. The limit of the rearward position to which the shaft is returned when the instrument is not activated is determined by the length of the spring when it is not compressed.

The inner shaft is provided with a lateral notch 26 spaced a distance d proximally from the sharp point 16 of the inner shaft, the purpose of moving the inner shaft forward relative to the outer shaft 12 being to expose the notch 26, as shown in FIG. 2. Preferably, the notch has a rectangular shape of predetermined width w, as shown in FIGS. 1 and 2. The distance d and the width w of the notch are chosen so that when the push button is released the notch is drawn entirely within the outer shaft, or sheath, and when the push button is fully depressed, the notch is entirely exposed.

In addition, a handle 28 is connected to the distal end of the outer shaft 12 to enable the user to grip the instrument. The handle is in the shape of an elongate, rectangular prism disposed symmetrically about the proximal end of the outer shaft 12. Also, the handle 28 is provided with a pair of proximally concave indentations 30 and 32, respectively, disposed on opposite sides of the shaft 12. That is, the distal side of the handle is indented in the proximal direction. These permit the user to place two fingers in the respective concave indentations and the thumb of the same hand of the user on the end of the push button 22 to manipulate the instrument. By pressing down on the thumb, the inner shaft is extended to expose the notch 26, thereby activating the instrument.

Turning to FIG. 3, as well as FIGS. 1 and 2, the sharp point preferably is formed by a cutting edge 34 extending from the distal tip of the shaft 14 along one side thereof rearwardly toward the proximal end of the shaft. The cutting edge may be formed by grinding the end of the inner shaft 14 to achieve the shape shown in FIGS. 1, 2 and 3.

Preferably, the inner shaft 14 is substantially solid clear through and made of a flexible metal suitable for surgical use. However, it is to be recognized that the shaft 14 need not be entirely solid, provided that it has sufficient rigidity and resiliency that it will flex to fit into position for use, yet return to its original shape and transmit adequate force from its proximal end to its distal end to cut and be pushed through the abdominal muscle. The outer shaft primarily serves as a sheath for the notch 26, and is preferably made of a suitable flexible material, such as plastic, so as to deform to allow a suture placed in the notch to be pulled into the outer shaft by the inner shaft. If the outer shaft material is relatively thick, as may be the case where plastic is used, the outer shaft should preferably have a taper 19 at the distal end to facilitate forcing the instrument through tissue.

It is to be recognized that other materials, a different type of handle and a different type of operating means for moving the inner shaft forward and backward may be used without departing from the principals of the invention.

The method of use of the instrument 10 is illustrated in FIGS. 4A and 4B. In those figures, an incision 36 in the abdomen 38 of a patient is shown. Along one side 40 of the incision four layers of tissue can be seen, that is, the epidermis 42, a layer of fat 44, a layer of muscle 46 and the peritoneum 47. The upper edge 48 of the epidermis is shown on the opposite side of the incision, along with the upper edge 50 and lower edge 51 of the muscle, by hidden lines.

Referring first to FIG. 4A, in use of the instrument, the distal end 18 is forced beneath the epidermis 42, into the fatty tissue 44 and through the muscle 46 and peritoneum 47, as shown at 52. The sharp point 16 starts a cut through the muscle tissue and peritoneum, which is completed by the cutting edge 34, providing a small opening adequate for receiving the outer shaft 12. Typically, the user would place a thumb or other finger on the push button 22 to keep the inner shaft 14 from being pushed further back into the outer shaft 12.

Referring back to FIGS. 1 and 2, in the first instance the push button 22 is depressed as shown in FIG. 2. A suture, such as suture 53 shown in FIG. 4A, is then placed in the notch 26. Thereafter, the push button 22 is released so that the spring 24 draws the inner shaft backward through the outer shaft 12 until the suture 52 is pulled back into the outer shaft 14 and gripped between the inner shaft 14 and the outer shaft 12, as shown in FIG. 4. It is to be recognized that, in FIG. 4A, the suture is shown gripped inside the abdomen, as explained hereafter, but that initially the suture would be gripped outside the abdomen to begin the suturing process.

Once the suture is gripped by the instrument, the instrument is forced through the muscle tissue 46, as previously explained, at a starting point for suturing the muscle. In FIG. 4A that starting point is shown at 54, where the suture 53 runs through the muscle tissue. Indeed, forcing the instrument 10 through the muscle tissue 46 also guides the suture through the resulting opening.

More specifically, the instrument is used as follows. After placing a suture 53 into the notch 26 and securing it by retracting the notch into the outer shaft, the instrument is grasped by the handle 28. The pointed end of the needle is placed through the incision in the skin and underlying fat, engaging the facial covering of the muscle on one side of the incision. Sufficient pressure is applied to force the needle through the fascia, muscle and peritoneum into the abdominal cavity. The suture 53 is then grasped by another grasping instrument 55, such as grasping forceps, inserted into the abdominal cavity through another incision, and the suture is released from the notch by extending the inner shaft so as to move the notch forward out of the sheath. The instrument is then removed from the wound, leaving the suture in place at 54 in FIG. 4A.

Thereafter, the instrument is reinserted on the opposite side of the muscle incision at 52 in FIG. 4A in the same way, except that the instrument is empty. The suture previously passed through the muscle, and now being held by the separate grasping instrument 55 is placed into the notch by the separate grasping instrument 55. The push button of the instrument is pressed to expose its notch 26, which is manipulated over the suture inside the abdomen, and the push button is released to grip the suture inside the abdomen, as shown in FIG. 4A. The instrument is then removed from the incision, bringing the suture with it. The suture has thereby been placed through the desired tissues and both ends exit the skin incision so that the suture is ready to be tied, as shown in FIG. 4B.

It is to be recognized that, while the procedure described above is the preferred method of using the instrument, variations in these steps might be used without departing from the principles of the invention.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

I claim:

1. A method for suturing muscle tissue of a patient at the site of a wound, comprising the steps of:
   (a) attaching a suture to a needle having a distal end and a proximal end, gripping means adjacent the distal end and operating means adjacent the proximal end for actuating the gripping means to grip said suture, said suture being attached to said needle by said gripping means;
   (b) forcing said needle through muscle tissue adjacent a first side of said wound so as to guide said suture therethrough;
   (c) after said suture has been guided through said muscle tissue in step (b), releasing said suture from said needle using said operating means;
   (d) forcing through muscle tissue adjacent a second side of said wound a needle having a distal end and a proximal end, gripping means adjacent the distal end and operating means adjacent the proximal end for actuating the gripping means to grip said suture;
   (e) gripping said suture within the body of the patient using the needle used in step (d); and
   (f) withdrawing the needle used in step (e) from said muscle tissue adjacent said second side of said wound so as to guide said suture from within the body of the patient therethrough.

2. The method of claim 1, further comprising the step of withdrawing said needle used in step (b) from said muscle tissue adjacent said first side of said wound.

3. The method of claim 1, wherein said needle comprises:
   (i) an elongate, hollow first shaft having a proximal end and a distal end;
   (ii) an elongate second shaft having a proximal end and a distal end disposed inside said first shaft, said second shaft terminating at the distal end thereof in a sharp point and having a lateral notch therein disposed a predetermined distance proximally from said distal end; and
   (iii) operating means disposed at the proximal end of said first shaft for moving said second shaft forward to position said notch beyond the distal end of said first shaft and for moving said second shaft backward to position said notch within the distal end of said first shaft.

4. The method of claim 3, wherein said operating means includes a spring connected to said first shaft and to said second shaft so as to apply backward force on said second shaft relative to said first shaft.

5. The method of claim 4, wherein said operating means includes actuation means for applying forward force on said second shaft relative to said first shaft to overcome said backward force and move said first shaft forward.

6. The method of claim 5, wherein said actuation means comprises a push attached to the proximal end of said second shaft.

7. The method of claim 6, further comprising a handle attached adjacent the proximal end of said first shaft.

8. The method of claim 7, wherein said handle comprises an elongate member extending laterally from said first shaft.

9. The method of claim 8, wherein said elongate member includes proximally-concave indentations on opposite sides of said first shaft for receiving first and second fingers, respectively, of the hand of a user so that the thumb of that hand may be used to depress said push button.

10. The method of claim 3, wherein said sharp point is formed by a v-shaped cutting edge extending from a point on one side of said second shaft to a position proximal therefrom on the opposite side of said second shaft.

11. The method of claim 10, wherein said notch is formed in said second shaft a predetermined distance proximally from said cutting edge and has a predetermined length.

12. The method of claim 11, wherein said operating means includes a spring connected to said first shaft and to said second shaft so as to apply backward force on said second shaft relative to said first shaft, and actuation means for applying forward force on said second shaft relative to said first shaft to overcome said backward force and move said first shaft forward sufficiently to expose said notch.

13. The method of claim 3, further comprising a handle attached adjacent the proximal end of said first shaft.

14. The method of claim 13, wherein said handle comprises an elongate member extending laterally from said first shaft.

15. The method of claim 14, wherein said elongate member includes proximally-concave indentations on opposite sides of said first shaft for receiving first and second fingers, respectively, of the hand of a user so that the thumb of that hand may be used to depress said push button.

16. The method of claim 13, wherein said operating means includes a spring connected to said first shaft and to said second shaft so as to apply backward force on said second shaft relative to said first shaft and a push button attached to the proximal end of said second shaft.

17. The method of claim 13, wherein said sharp point is formed by a v-shaped cutting edge extending from a point on one side of said second shaft to a position proximal therefrom on the opposite side of said second shaft.

18. The method of claim 3, wherein said operating means includes a spring connected to said first shaft and to said second shaft so as to apply backward force on said second shaft relative to said first shaft and a push button attached to the proximal end of said second shaft.

19. The method of claim 3, wherein, said first shaft is made of a flexible material.

20. The method of claim 3, wherein said second shaft is substantially solid and flexible.

21. The method of claim 1, further comprising, between steps (c) and (d), the steps of (i) gripping said suture within the body of the patient using a separate gripping means inserted into the body, and (ii) withdrawing said needle from said muscle tissue adjacent said first side of said wound.

22. A method for suturing muscle tissue of a patient at the site of a wound, comprising the steps of:

(a) attaching a suture to a needle having a distal end and a proximal end, gripping means adjacent the distal end and operating means adjacent the proximal end for actuating the gripping means to grip said suture, said suture being attached to said needle by said gripping means;

(b) forcing said needle through muscle tissue adjacent a first side of said wound so as to guide said suture therethrough;

(c) after said suture has been guided through said muscle tissue in step (b), releasing said suture from said needle using said operating means;

(d) withdrawing said needle from said muscle tissue adjacent said first side of said wound after said suture has been released in step (c);

(e) forcing said needle through muscle tissue adjacent a second side of said would and gripping said suture within the body of the patient using said needle; and (f) withdrawing said needle from said muscle tissue adjacent said second side of said wound so as to guide said suture from within the body of the patient therethrough.

23. The method of claim 22, wherein steps (a) through (f) are repeated until the muscle tissue at the wound is substantially closed, the portion of the suture guided through the muscle tissue in step (f) the suture thereafter being guided through the muscle tissue in step (a).

24. The method of claim 22, wherein said needle comprises:

(i) an elongate, hollow first shaft having a proximal end and a distal end;

(ii) an elongate second shaft having a proximal end and a distal end disposed inside said first shaft, said second shaft terminating at the distal end thereof in a sharp point and having a lateral notch therein disposed a predetermined distance proximally from said distal end; and (iii) operating means disposed at the proximal end of said first shaft for moving said second shaft forward to position said notch beyond the distal end of said first shaft and for moving said second shaft backward to position said notch within the distal end of said first shaft.

25. A method for suturing muscle tissue of a patient at the site of a wound, comprising the steps of:

(a) attaching a suture to a needle having a distal end and a proximal end, gripping means adjacent the distal end and operating means adjacent the proximal end for actuating the gripping means to grip said suture, said suture being attached to said needle by said gripping means;

(b) forcing said needle through muscle tissue adjacent a first side of said wound so as to guide said suture therethrough;

(c) after said suture has been guided through said muscle tissue in step (b), releasing said suture from said needle using said operating means;

(d) gripping said suture within the body of the patient using a separate gripping means inserted into the body; and (e) withdrawing said needle from said muscle tissue adjacent said first side of said wound.

* * * * *